United States Patent
Ogawa et al.

(10) Patent No.: US 8,253,103 B2
(45) Date of Patent: Aug. 28, 2012

(54) TERAHERTZ WAVE MEASURING APPARATUS HAVING SPACE ARRANGEMENT STRUCTURE AND MEASURING METHOD

(75) Inventors: Yuichi Ogawa, Miyagi (JP); Shinichiro Hayashi, Miyagi (JP); Eiji Kato, Tokyo (JP)

(73) Assignee: Advantest Corporation, Tokyo (JP)

(*) Notice: Subject to any disclaimer, the term of this patent is extended or adjusted under 35 U.S.C. 154(b) by 0 days.

(21) Appl. No.: 12/511,016

(22) Filed: Jul. 28, 2009

(65) Prior Publication Data
US 2010/0025586 A1   Feb. 4, 2010

Related U.S. Application Data

(63) Continuation of application No. PCT/JP2008/051404, filed on Jan. 30, 2008.

(30) Foreign Application Priority Data

Jan. 31, 2007 (JP) ................... 2007-021660

(51) Int. Cl.
*G01J 1/00* (2006.01)
*G01J 5/00* (2006.01)

(52) U.S. Cl. .................. 250/336.1; 250/338.1

(58) Field of Classification Search ............... 250/336.1, 250/338.1–339.12
See application file for complete search history.

(56) References Cited

U.S. PATENT DOCUMENTS

| | | | |
|---|---|---|---|
| 5,973,316 A | 10/1999 | Ebesen et al. | |
| 6,052,238 A | 4/2000 | Ebesen et al. | |
| 6,078,047 A * | 6/2000 | Mittleman et al. | 250/338.1 |
| 7,498,577 B2 * | 3/2009 | Kurosaka et al. | 250/339.05 |
| 7,551,269 B2 * | 6/2009 | Itsuji | 356/51 |
| 7,649,633 B2 * | 1/2010 | Kawate | 356/504 |
| 7,683,325 B2 * | 3/2010 | Sekiguchi et al. | 250/339.06 |
| 7,781,736 B2 * | 8/2010 | Logan et al. | 250/339.07 |
| 7,795,582 B2 * | 9/2010 | Jez et al. | 250/336.1 |
| 2004/0061055 A1 * | 4/2004 | Kawase et al. | 250/330 |
| 2005/0253071 A1 * | 11/2005 | Ferguson et al. | 250/341.1 |
| 2006/0043298 A1 * | 3/2006 | Kawase et al. | 250/339.06 |
| 2006/0054824 A1 * | 3/2006 | Federici et al. | 250/339.02 |

(Continued)

FOREIGN PATENT DOCUMENTS

JP        11-072607 A       3/1999

(Continued)

OTHER PUBLICATIONS

International Search Report (ISR) for PCT/JP2008/051404 for Examiner consideration, citing U.S. Patent Application Nos. 1-2 and Foreign Patent Document Nos. 1-2 listed above.

(Continued)

*Primary Examiner* — David Porta
*Assistant Examiner* — Casey Bryant
(74) *Attorney, Agent, or Firm* — Chen Yoshimura LLP

(57) ABSTRACT

There is provided a measuring apparatus including a space arrangement structure that includes space regions surrounded by conductors in a plane, an electromagnetic wave emitter that emits electromagnetic waves towards an object held by the space arrangement structure, and an electromagnetic wave detector that measures the electromagnetic waves that have passed through the space arrangement structure. Here, characteristics of the object are measured by measuring the electromagnetic waves that have passed through the space arrangement structure. The electromagnetic waves emitted from the electromagnetic wave emitter towards the space arrangement structure are incident on the plane containing the space regions at an angle, and the electromagnetic waves that have passed through the space arrangement structure are measured.

14 Claims, 11 Drawing Sheets

U.S. PATENT DOCUMENTS

| | | | | |
|---|---|---|---|---|
| 2006/0237650 | A1* | 10/2006 | Taday | 250/339.11 |
| 2007/0229094 | A1* | 10/2007 | Kasai et al. | 324/639 |
| 2008/0239317 | A1* | 10/2008 | Schulkin et al. | 356/365 |

FOREIGN PATENT DOCUMENTS

| | | |
|---|---|---|
| JP | 2004-108905 A | 4/2004 |
| JP | 2004-117703 A | 4/2004 |
| JP | 2007010366 A | 1/2007 |

OTHER PUBLICATIONS

Written Option (PCT/ISA/237) of PCT/JP2008/051404.

Sakai, "Terahertz Time-Domain Spectroscopy", Spectroscopy Studies, vol. 50, No. 6, pp. 261-273, 2001, Kobe, Japan. Mentioned on p. 1 of as-filed specification as concise explanation of relevance.

Lamarre et al., "Metallic Mesh Properties and Design of Submillimeter Filters", International Journal of Infrared and Millimeter Waves, vol. 2, No. 2, 1981, pp. 273-292. Cited in ISR and mentioned on p. 2 of as-filed specification.

Ogawa et al., "Usugata Kinzoku Mesh no Toka Tokusei O Riyo shita Sensor Oyo", Dai 67 Kai Exended abstracts; The Japan Society of Applied Physics, Aug. 29, 2006, Dai 67 Kai, separate vol. 3, p. 1016, 31p-za-2. Cited in ISR as concise explanation of relevance.

Yoshida et al., "Kinzoku Mesh ni yoru Tanpakushitsu no Label Free Kenshutsu", IEICE Technical Report, Nov. 20, 2007, vol. 107, No. 355, p. 99-102. Cited in ISR as concise explanation of relevance.

Yoshida et al., "Terahertz sensing method for protein detection using a thin metallic mesh", Applied Physics Letters, Dec. 17, 2007, vol. 91, No. 25, p. 253901-1-p. 253901-3. Cited in ISR.

Ogawa et al., "Printable Mesh O Mochiita Terahertz-tai Kussetsuritsu Sensor", Dai 66 Kai Extended abstracts; the Japan Society of Applied Physics, Sep. 7, 2005, Dai 66 Kai, separate vol. 3, p. 966, 9a-P6-26. Cited in ISR as concise explanation of relevance.

Japanese Office Action dated Sep. 20, 2011, in a counterpart Japanese patent application No. 2007-021660, citing JP 2007-010366, JP H11-072607 and Lamarre et al., "Metallic Mesh Properties and Design of Submillimeter Filters", Ogawa et al., "Usugata Kinzoku Mesh no Toka Tokusei O Riyo shita Sensor Oyo", and Ogawa et al., "Printable Mesh O Mochiita Terahertz-tai Kussetsuritsu Sensor", which have been submitted in a previous IDS. A machine translation (not reviewed for accuracy) attached.

Japanese Office Action dated Apr. 3, 2012, in a counterpart Japanese patent application No. 2007-021660.

\* cited by examiner

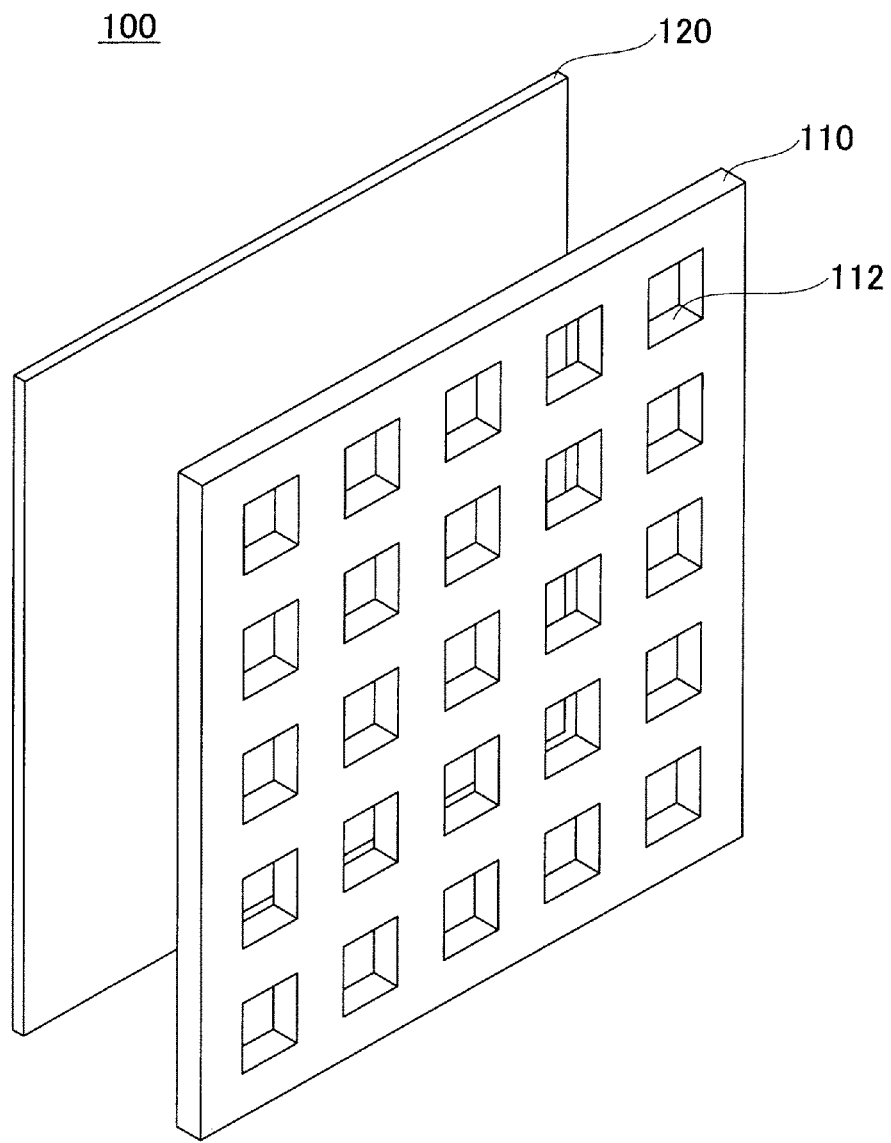
F I G . 1

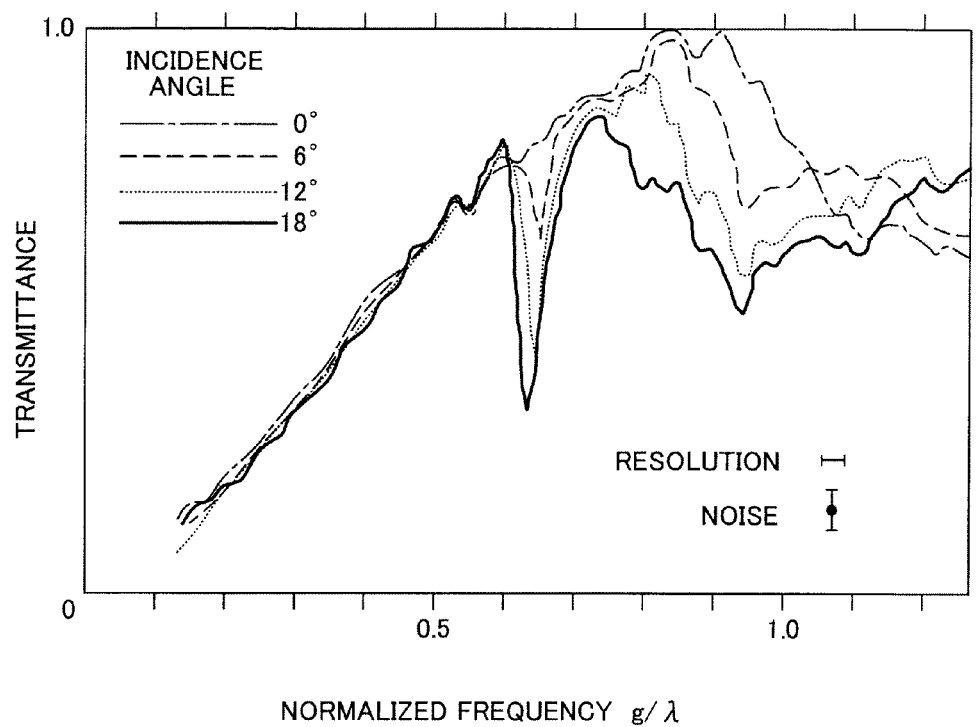
F I G . 5

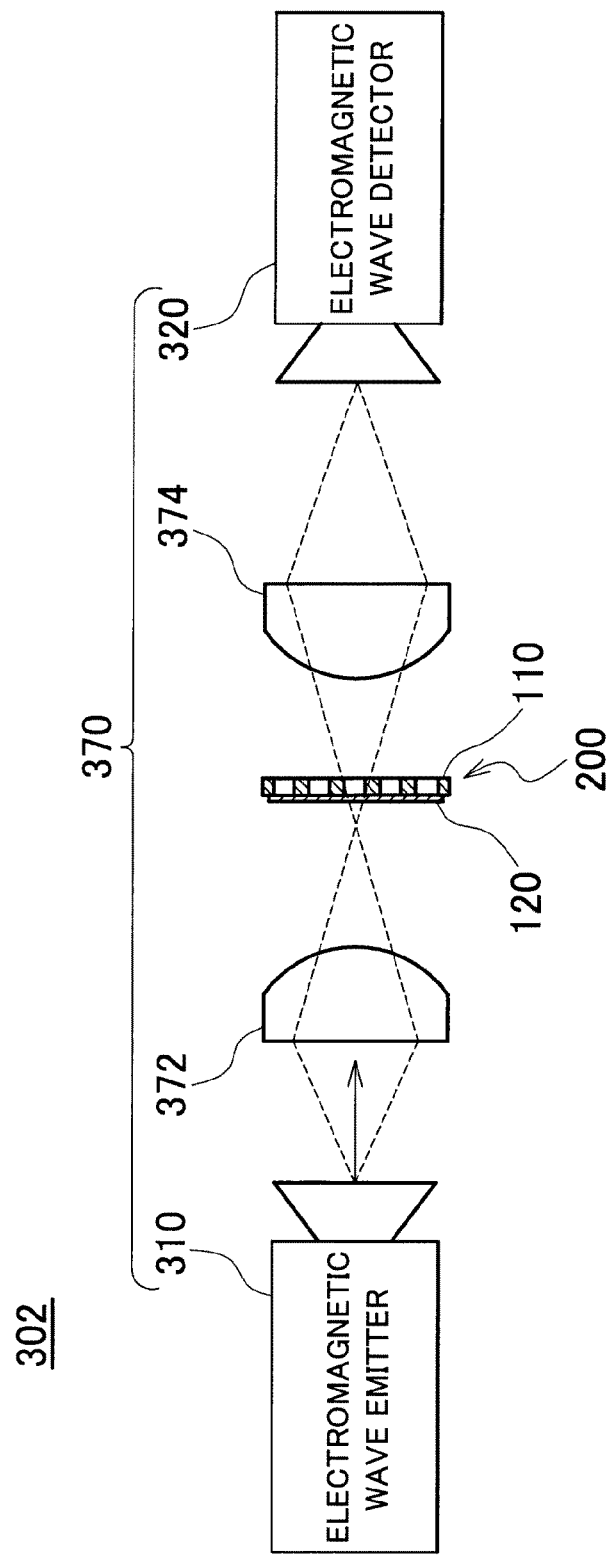
F I G . 6

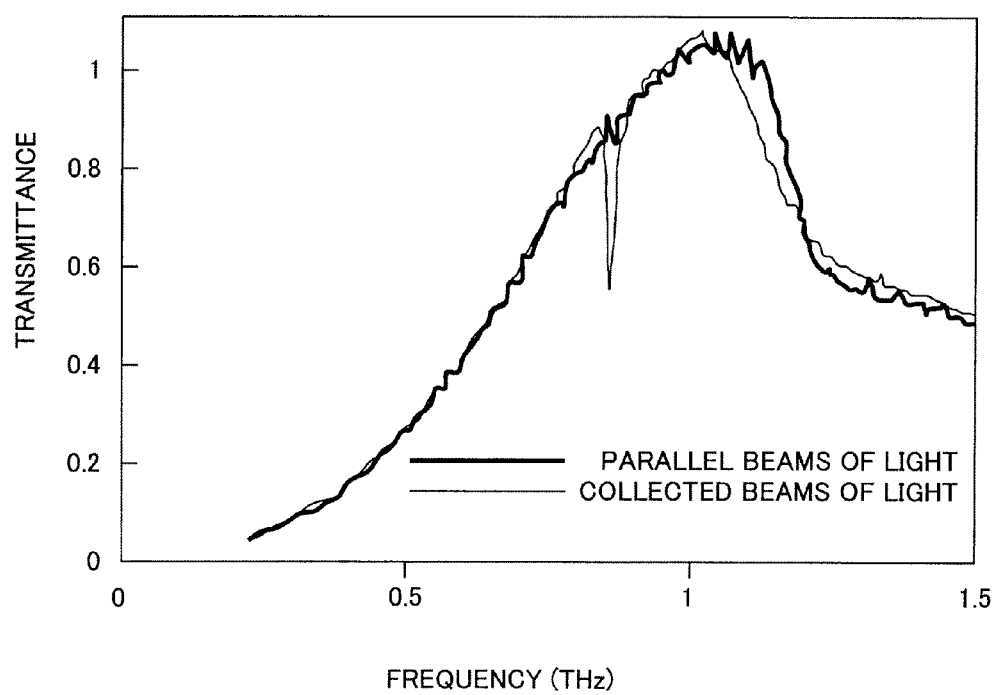
F I G . 7

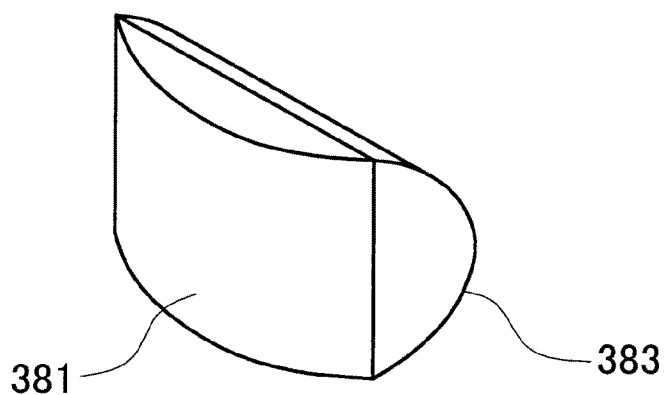
F I G. 11

TERAHERTZ WAVE MEASURING APPARATUS HAVING SPACE ARRANGEMENT STRUCTURE AND MEASURING METHOD

CROSS REFERENCE TO RELATED APPLICATION

This is a continuation application of PCT/JP2008/051404 filed on Jan. 30, 2008, which claims priority from a Japanese Patent Application(s) NO. 2007-021660 filed on Jan. 31, 2007, the contents of which are incorporated herein by reference.

BACKGROUND

1. Technical Field

The present invention relates to a measuring apparatus and a measuring method. More particularly, the present invention relates to an apparatus and a method for measuring a characteristic of an object by irradiating the object with an electromagnetic wave and measuring the modulated electromagnetic wave from the object.

2. Related Art

Electromagnetic waves whose frequency substantially falls within a range from 20 GHz to 120 THz or whose wavelength substantially falls within a range of 1.5 cm to 2.5 μm (hereinafter, referred to as "terahertz waves") appear at the boundary between light and radio waves. The terahertz waves have not been used very much in any technical fields. Applications of terahertz waves, however, have been increasingly considered in many technical fields due to the following achievements. It has become possible to generate short femtosecond terahertz pulses with the use of semiconductor lasers and a technique based on such pulses, which is referred to as terahertz time domain spectroscopy, has been developed.

"Terahertz Time Domain Spectroscopy", Kiyomi SAKAI, Spectroscopy Studies, Vol. 50, No. 6, Page. 261-273 (2001) discusses the principles of the spectroscopic measurement, imaging, and any other applications using electromagnetic waves in the terahertz band. As mentioned in Non-Patent Document 1, terahertz waves have both a transmittance property similarly to radio waves and a line-of-sight propagation property similarly to light. Thus, the terahertz light can exhibit high resolution while being able to pass through objects and be handled in quasi-optical devices such as lenses and mirrors.

Japanese Patent Application Publication No. 2004-108905 mentioned below discloses a method for detecting the shape, composition and any other characteristics of an object by irradiating the object with terahertz waves having different wavelengths and measuring the transmittance values of the object for these terahertz waves to know the electromagnetic wave absorption by the object. This method can detect any objects that have wavelength dependence of terahertz wave absorption without relying on the surfaces of objects.

J. M. Lamarre et al., "METALLIC MESH PROPERTIES AND DESIGN OF SUBMILLIMETER FILTERS," Int. Jnl. Of Infrared and Millimeter Waves, Vol. 2, No. 2, 1981, pp. 273-292 and Japanese Patent Application Publication No. 2004-117703 state that a metal plate having periodically arranged spaces (hereinafter referred to as "the space arrangement structure") excellently transmits electromagnetic waves. This space arrangement structure can be utilized as a retarder by itself, and also used as a support for an object to be measured during measurement using terahertz waves.

When irradiated with terahertz waves, an object to be measured returns a measurement result uniquely determined by the characteristics of the object. For example, when the transmittance of the object is measured, the frequency characteristics of the transmittance of the object have a peak indicating a local maximal value that is uniquely determined by the characteristics of the object.

In light of the above, it is possible to know the characteristics of an object by first measuring the characteristics of a space arrangement structure alone, then measuring the characteristics of a combined structure in which the object is supported by the space arrangement structure, and finally calculating the difference between the measured characteristics. When the frequency characteristics of the transmittance of the object are measured as mentioned above, for example, the peak appears in different bands. In this manner, it is possible to detect whether or not the object is present and may also be possible to identify the composition and any other characteristics of the object depending on the shift of the peak. Since such a change in the measurement results is clearly found, effective and valid measurement is possible even when the quantity of the object is very small.

When measured by using terahertz waves, however, the frequency characteristics of transmittance draw a relatively smooth and continuous curve. Therefore, there are difficulties in detecting a shift when only a small shift is caused by presence of an object. In light of the above, it is desired to provide a measuring method and a measuring apparatus that are capable of detecting the characteristics of an object with more ease with it being possible to maintain the advantages of the measurement using terahertz wave.

SUMMARY

Therefore, it is an object of an aspect of the innovations herein to provide a measuring apparatus and a measuring method which are capable of overcoming the above drawbacks accompanying the related art. The above and other objects can be achieved by combinations described in the independent claims. The dependent claims define further advantageous and exemplary combinations of the innovations herein.

According to the first aspect related to the innovations herein, one exemplary measuring apparatus includes a space arrangement structure that includes space regions surrounded by conductors in a plane, an electromagnetic wave emitter that emits electromagnetic waves towards an object held by the space arrangement structure, and an electromagnetic wave detector that measures the electromagnetic waves that have passed through the space arrangement structure. Here, characteristics of the object are measured by measuring the electromagnetic waves that have passed through the space arrangement structure. The electromagnetic waves emitted from the electromagnetic wave emitter towards the space arrangement structure are incident on the plane containing the space regions at an angle, and the electromagnetic waves that have passed through the space arrangement structure are measured.

According to the second aspect related to the innovations herein, one exemplary test module provides a measuring method using a space arrangement structure that includes space regions surrounded by conductors in a plane, an electromagnetic wave emitter that emits electromagnetic waves towards an object held by the space arrangement structure, and an electromagnetic wave detector that measures the electromagnetic waves that have passed through the space arrangement structure. The electromagnetic wave emitter emits the electromagnetic waves that are incident on a plane containing the space regions at an angle, and characteristics of the object are detected by measuring the electromagnetic waves that have passed through the space arrangement structure.

The summary clause does not necessarily describe all necessary features of the embodiments of the present invention. The present invention may also be a sub-combination of the features described above. The above and other features and advantages of the present invention will become more apparent from the following description of the embodiments taken in conjunction with the accompanying drawings.

BRIEF DESCRIPTION OF THE DRAWINGS

FIG. 1 is an exploded perspective view illustrating the shape of a support 100 that supports an object 210 in a measuring apparatus 300.

FIG. 5 is a graph showing the variation of the frequency characteristics of the prepared slide 200, which is caused by the variation of the incidence angle α of the terahertz waves.

FIG. 6 schematically illustrates the configuration of an optical system 370 in a measuring apparatus 302 relating to a different exemplary embodiment.

FIG. 7 is a graph showing the frequency characteristics of transmittance measured by using the measuring apparatus 302, in comparison with the frequency characteristics of transmittance measured by using parallel beams of light.

FIG. 11 is a perspective view illustrating the shapes of compound lenses 382 and 384 used in the measuring apparatus 304 shown in FIG. 10.

DESCRIPTION OF EXEMPLARY EMBODIMENT

Figure 2:
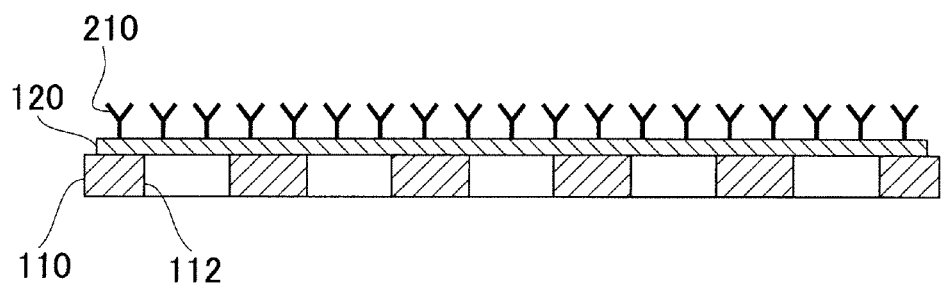
FIG. 2 is a cross-sectional view illustrating the configuration of a prepared slide 200 using the support 100 shown in FIG. 1.

Some aspects of the invention will now be described based on the embodiments, which do not intend to limit the scope of the present invention, but exemplify the invention. All of the features and the combinations thereof described in the embodiment are not necessarily essential to the invention.

First Embodiment

FIG. 1 is a perspective view illustrating the configuration of a support 100 that supports an object 210 to be measured (not shown in FIG. 1) in a measuring apparatus 300 described later. As shown in FIG. 1, the support 100 is formed by combining together a space arrangement structure 110 and a support film 120.

The space arrangement structure 110 is a plate made of a conductive material such as metal and has a plurality of spaces 112 that are arranged at even intervals. Such a mesh conductive plate has transmittance exceeding its aperture area ratio for electromagnetic waves. Therefore, the space arrangement structure 110 allows electromagnetic waves such as terahertz waves to pass through at a high rate while supporting the object 210.

The space arrangement structure 110 can be made of any conductive material, which is not limited to metal. The space arrangement structure 110 produces predetermined effects of high transmittance of electromagnetic waves, as long as the spaces 112 are respectively surrounded by conductors. The shape of the spaces 112 is not limited to a square, as long as the respective spaces 112 have any symmetrical figures. The arrangement of the spaces 112 is not limited to the matrix arrangement as shown in FIG. 1, as long as the spaces 112 are regularly or periodically arranged. The number of spaces 112 is not limited to any particular value, as long as there are one or more spaces 112. Thus, the material and configuration of the space arrangement structure 110 may be selected from a wide range of options depending on the type of the object 210, measurement conditions and any other factors.

Note that, however, the size of the spaces 112 is preferably no less than 0.3 times and no more than twice as large as the wavelength of an electromagnetic wave used for measurement. When the size of the spaces 112 falls below this range, the space arrangement structure 110 exhibits significantly lowered transmittance for electromagnetic waves. When the size of the spaces 112 exceeds this range, the space arrangement structure 110 does not produce later-described effects on the electromagnetic waves.

The support film 120 is used to hold a minute object 210 or a small amount of object 210 such as a powder onto the surface of the space arrangement structure 110 having the spaces 112. Therefore, the support film 120 is preferably as thin as possible, provided that the support film 120 is sufficiently strong to be able to support the object 210, and made of a material that does not prevent electromagnetic waves used for measurement from being transmitted. Specifically speaking, the support film 120 may be formed by using polyamide resin film or the like. This enables a small amount of protein or the like to be measured. The support film 120 may be replaced with an airtight or liquid-tight container, so that a substance dispersed in a fluid can be measured.

FIG. 2 is a cross-sectional view illustrating the configuration of a prepared slide 200 that uses the support 100 shown in FIG. 1. As shown in FIG. 2, the support film 120 is applied to the surface of the space arrangement structure 110, and the object 210 is attached to the support film 120. In this manner, even when having a smaller size than the spaces 112, the object 210 can be attached to the surface of the space arrangement structure 110. The result is referred to as the prepared slide 200. The prepared slide 200 can be easily handled, for example, loaded onto the measuring apparatus 300.

Figure 3:
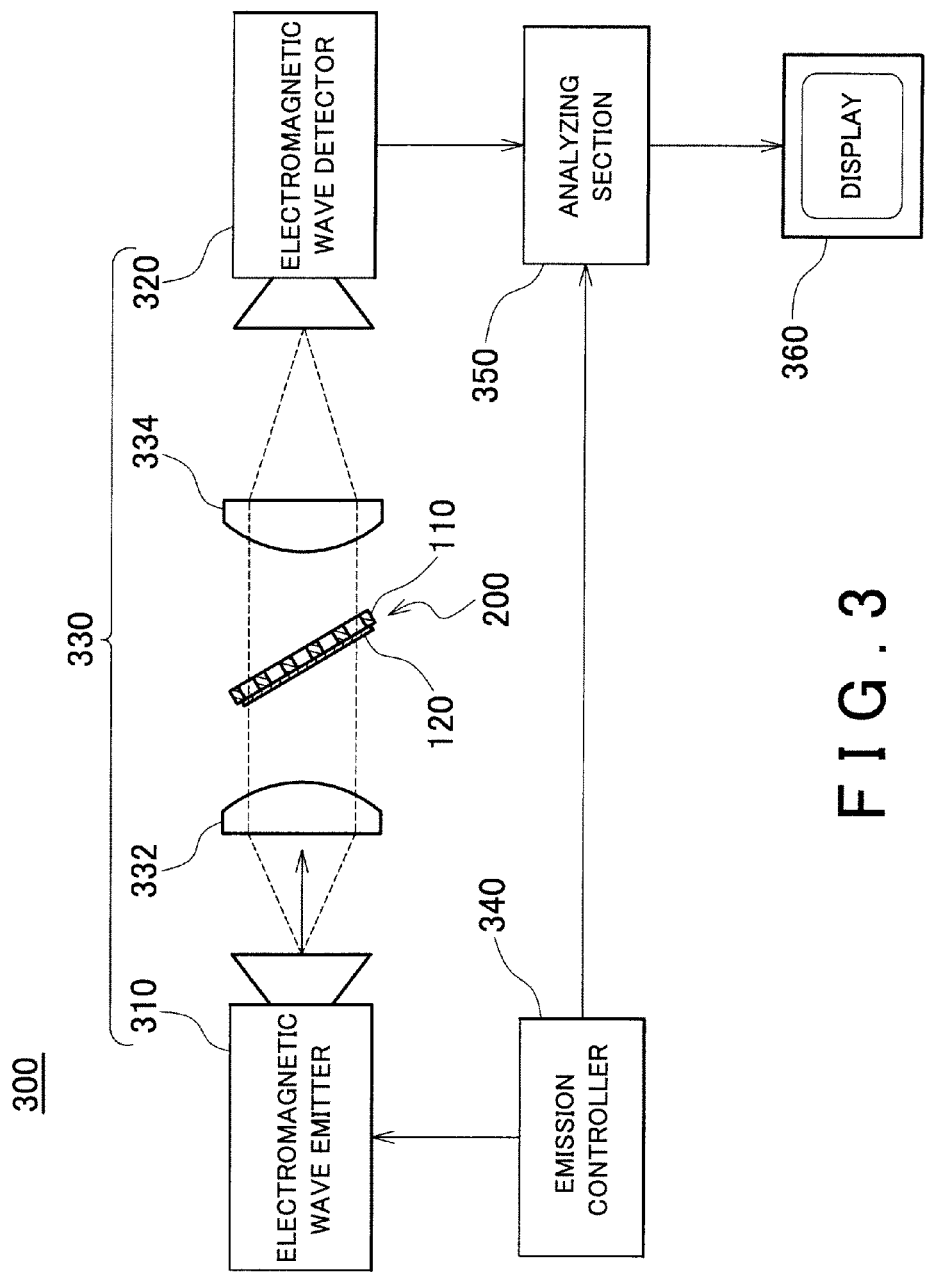
FIG. 3 schematically illustrates the overall configuration of the measuring apparatus 300 and the position of the prepared slide 200 in the measuring apparatus 300.

FIG. 3 schematically illustrates the overall configuration of the measuring apparatus 300 and the position of the prepared slide 200 in the measuring apparatus 300. As shown in FIG. 3, the measuring apparatus 300 includes an optical system 330 formed between an electromagnetic wave emitter 310 that generates and emits electromagnetic waves and an electromagnetic wave detector 320 that detects the emitted electromagnetic waves. The optical system 330 includes a pair of collimating lenses 332 and 334. Here, the electromagnetic waves used in the measuring apparatus 300 are in a wavelength band that exhibits optical characteristics such as line-of-sight propagation property and can be handled by optical elements such as lenses and mirrors. Therefore, the expression "optical system 330" is used for the sake of convenience.

The measuring apparatus 300 further includes an emission controller 340 that controls the operations of the electromagnetic wave emitter 310, an analyzing section 350 that analyzes the results of the detection done by the electromagnetic wave detector 320, and a display 360 that displays the results of the analysis done by the analyzing section 350. The emission controller 340 is also coupled to the analyzing section 350 for the purpose of detection timing synchronization.

The electromagnetic wave emitter 310 having the above-described configuration generates terahertz waves based on optical rectification effects of electro-optical crystals such as ZnTe by using a short optical pulse laser as a light source under the control of the emission controller 340. The electromagnetic waves emitted from the electromagnetic wave emitter 310 are converted into parallel beams of light by the collimating lens 332 and then sent to the collimating lens 334. The electromagnetic waves then enter the collimating lens 334 and are converged towards the light receptor of the electromagnetic wave detector 320. The electromagnetic waves are then detected by the electromagnetic wave detector 320 and converted into an electrical signal, which is sent to the analyzing section 350 and visibly displayed on the display 360 in the form of, for example, frequency characteristics of transmittance.

The prepared slide 200 is held by a holder (not shown) that is positioned between the collimating lens 332 and 334, so as to be exposed to the electromagnetic waves, or the parallel beams of light. Here, the prepared slide 200 is disposed at an angle with respect to the optical axis of the optical system 330. Therefore, the electromagnetic waves emitted from the electromagnetic wave emitter 310 obliquely passes through the prepared slide 200 before detected by the electromagnetic wave detector 320.

Figure 4:
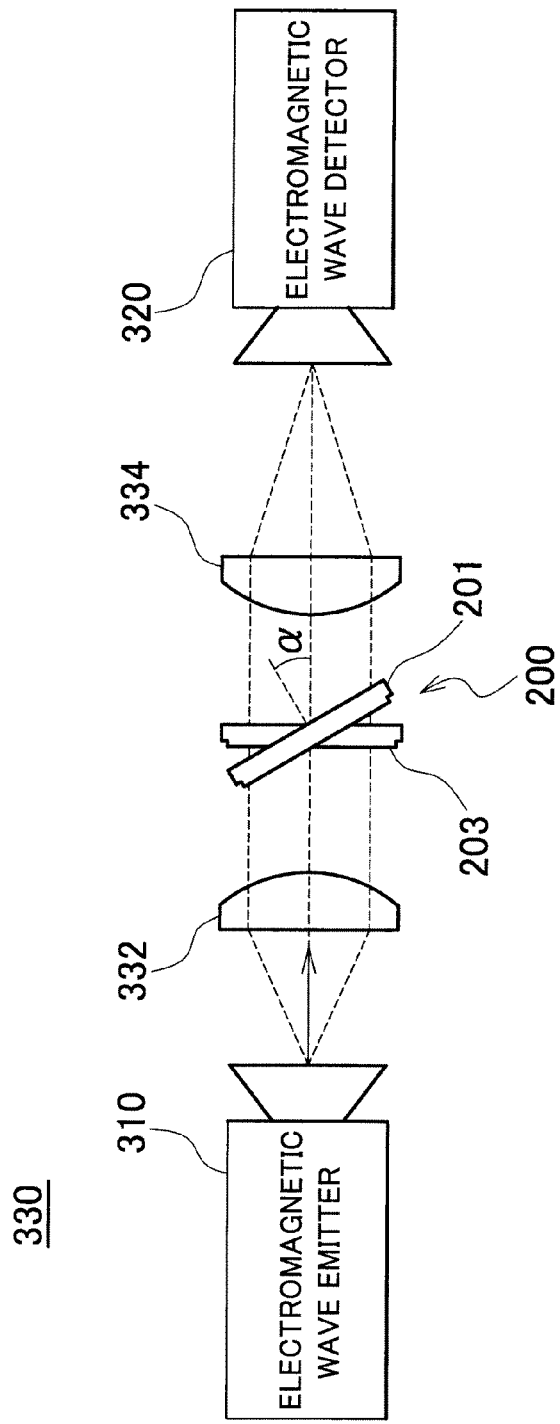
FIG. 4 illustrates the definition of an incidence angle α of terahertz waves incident on the prepared slide 200 in an optical system 330 of the measuring apparatus 300.

FIG. 4 illustrates the definition of the incidence angle of the terahertz waves incident on the prepared slide 200 in the optical system 330 of the measuring apparatus 300. As shown in FIG. 4, the incidence angle $\alpha$ is defined as an angle formed between a straight line that is orthogonal to the plane in which the spaces 112 are arranged in the space arrangement structure 110 and the optical axis of the optical system 330 formed in the measuring apparatus 300.

FIG. 5 is a graph showing the variation of the frequency characteristic of the transmittance, which is caused by the variation of the incidence angle $\alpha$ of the terahertz waves incident on the prepared slide 200. This graph is cited from the above-mentioned document J. M. Lamarre et al., "METALLIC MESH PROPERTIES AND DESIGN OF SUBMILLIMETER FILTERS." As shown in FIG. 5, when the electromagnetic wave emitter 310 emits electromagnetic waves to the prepared slide 200 and the electromagnetic wave detector 320 receives and measures the resulting electromagnetic waves, the frequency characteristics of the electromagnetic wave transmittance has a peak at which the transmittance takes a local maximal value. Furthermore, when the angle of the prepared slide 200 is varied from a prepared slide 203 that is orthogonal to the optical axis of the optical system 330 to a prepared slide 201 that has the incidence angle $\alpha$ with respect to the optical axis of the optical system 330, a single dip occurs relatively in the vicinity of the peak in the frequency characteristics. The dip becomes deeper and steeper as the incidence angle $\alpha$ increases.

It should be noted here that the transmittance of the space arrangement structure 110 for the electromagnetic waves significantly drops if the incidence angle $\alpha$ excessively increases and the electromagnetic wave emitter 310 cannot see the electromagnetic wave detector 320 through the spaces 112. Considering this, the incidence angle $\alpha$ is determined so as to fall within such a range that the space arrangement structure 110 maintains sufficiently high transmittance for the electromagnetic waves. Specifically speaking, the incidence angle $\alpha$ is set no more than 10 degrees, preferably approximately several degrees.

Since a sharp dip occurs in the frequency characteristics obtained as a result of the measurement as described above, it can be very easy to identify a change in the measurement result. Here, a dip is purposefully generated in the frequency characteristics to easily detect a change. The overall shape of the frequency characteristics, however, is not affected by the dip and can be read correctly since the dip only has a narrow width.

As described earlier, the space arrangement structure 110 holding the object 210 thereon can be positioned between the electromagnetic wave emitter 310 and the electromagnetic wave detector 320 in such a manner that the plane containing the spaces 112 is at an angle with respect to the straight line connecting together the electromagnetic wave emitter 310 and the electromagnetic wave detector 320. With such a configuration, the result of the measurement has a sharp dip in a particular band. By utilizing this dip as an indicator, a change caused in the measurement result by the property of the object 210 can be easily and accurately read.

According to the above-described configuration, a measuring method is provided which utilizes the space arrangement structure 110 that has the spaces 112 surrounded by conductors in a single plane, the electromagnetic wave emitter 310 that emits electromagnetic waves to the object 210 held on the surface of the space arrangement structure 110, and the electromagnetic wave detector 320 that measures the electromagnetic waves that have been emitted from the electromagnetic wave emitter 310 to the space arrangement structure 110 and have passed through the space arrangement structure 110, in order to irradiate the space arrangement structure 110 with the electromagnetic waves from the electromagnetic wave emitter 310 at the incidence angle $\alpha$ with respect to the plane containing the spaces 112, measure the electromagnetic waves that have passed through a space containing the spaces 112 and the object 210, and detect the characteristics of the object 210 by referring to a shift of a dip waveform in the measured frequency characteristics. This measuring method makes it possible to easily detect a shift in the measurement result. As a result, many different technical fields can take advantage of the measuring method for the object 210 that uses terahertz waves having both transmittance and line-of-sight propagation.

In addition, there is provided the measuring apparatus 300 including the space arrangement structure 110 that has the spaces 112 surrounded by conductors in a single plane, the electromagnetic wave emitter 310 that emits electromagnetic waves to the object 210 held on the surface of the space arrangement structure 110, and the electromagnetic wave detector 320 that measures the electromagnetic waves that have been emitted from the electromagnetic wave emitter 310 to the space arrangement structure 110 and have passed through the space arrangement structure 110. The measuring apparatus 300 is designed to measure the characteristics of the object 210 by measuring the electromagnetic waves that have passed through a space including the spaces 112 and the object 210. In the measuring apparatus 300, the electromagnetic waves that are emitted to the space arrangement structure 110 from the electromagnetic wave emitter 310 have the incidence angle $\alpha$ with respect to the plane including the spaces 112. The measuring apparatus 300 detects the characteristics of the object 210 by referring to a shift of a dip waveform in the measured frequency characteristics. In this manner, an apparatus that performs the above-described measuring method is provided.

Second Embodiment

FIG. 6 illustrates the optical structure of a measuring apparatus 302 relating to a different exemplary embodiment. Since the electromagnetic wave emitter 310, electromagnetic wave detector 320, analyzing section 350, and display 360 have the same configurations as in the measuring apparatus 300, FIG. 6 does not show some of these constituents.

As shown in FIG. 6, the measuring apparatus 302 is different from the measuring apparatus 300 shown in FIG. 3 in that an optical system 370 has light collecting lenses 372 and 374 in place of the collimating lenses 332 and 334. With such a configuration, the electromagnetic waves are incident on the space arrangement structure 110 of the measuring apparatus 302 at an angle, except for an electromagnetic wave on the optical axis. Apart from this feature, the measuring apparatus 302 is the same as the measuring apparatus 300 shown in FIG. 3, and the explanation is not repeated here.

FIG. 7 is a graph showing the frequency characteristics of the transmittance of the object 210, which is measured by using the converged beams of light in the measuring apparatus 302. For the comparison purposes, the graph also shows the frequency characteristics obtained when the same object 210 is measured by using parallel beams of light in the optical system 330 of the measuring apparatus 300 shown in FIG. 3.

As seen from FIG. 7, the result of the measurement shows an evident dip even though the space arrangement structure 110 is orthogonal to the optical axis of the optical system 380 formed between the electromagnetic wave emitter 310 and the electromagnetic wave detector 320. This is because the converged beams of light are incident on the space arrangement structure 110 at an angle. Thus, the measuring apparatus 302 can easily identify a slight change in frequency characteristics, which is caused by the object 210 that is, along with the space arrangement structure 110, irradiated with the electromagnetic waves. Note that an evident dip still occurs in the measured frequency characteristics even when the prepared slide 200 is moved in the direction of the optical axis of the optical system 370 so that the object 210 is positioned on the focus of the optical system 370.

In the above-described measuring apparatus 302, the space arrangement structure 110 holding the object 210 thereon is positioned between the electromagnetic wave emitter 310 and the electromagnetic wave detector 320 in such a manner that the plane containing the spaces 112 is orthogonal to the straight line connecting together the electromagnetic wave emitter 310 and the electromagnetic wave detector 320, and the electromagnetic waves emitted from the electromagnetic wave emitter 310 are converged towards a single point on the straight line. With such a configuration, while the space arrangement structure 110 can be arranged so as to extend vertically, the electromagnetic waves are incident on the space arrangement structure 110 at an angle, except for an electromagnetic wave on the optical axis. Consequently, it is possible to easily identify a change in the measurement result. The measuring apparatus 302 can be realized by replacing the collimating lenses 332 and 334 in the measuring apparatus 300 with the light collecting lenses 372 and 374. Thus, the above-described advantage can be made without changing the layout of the measuring apparatus 300.

Figure 8:
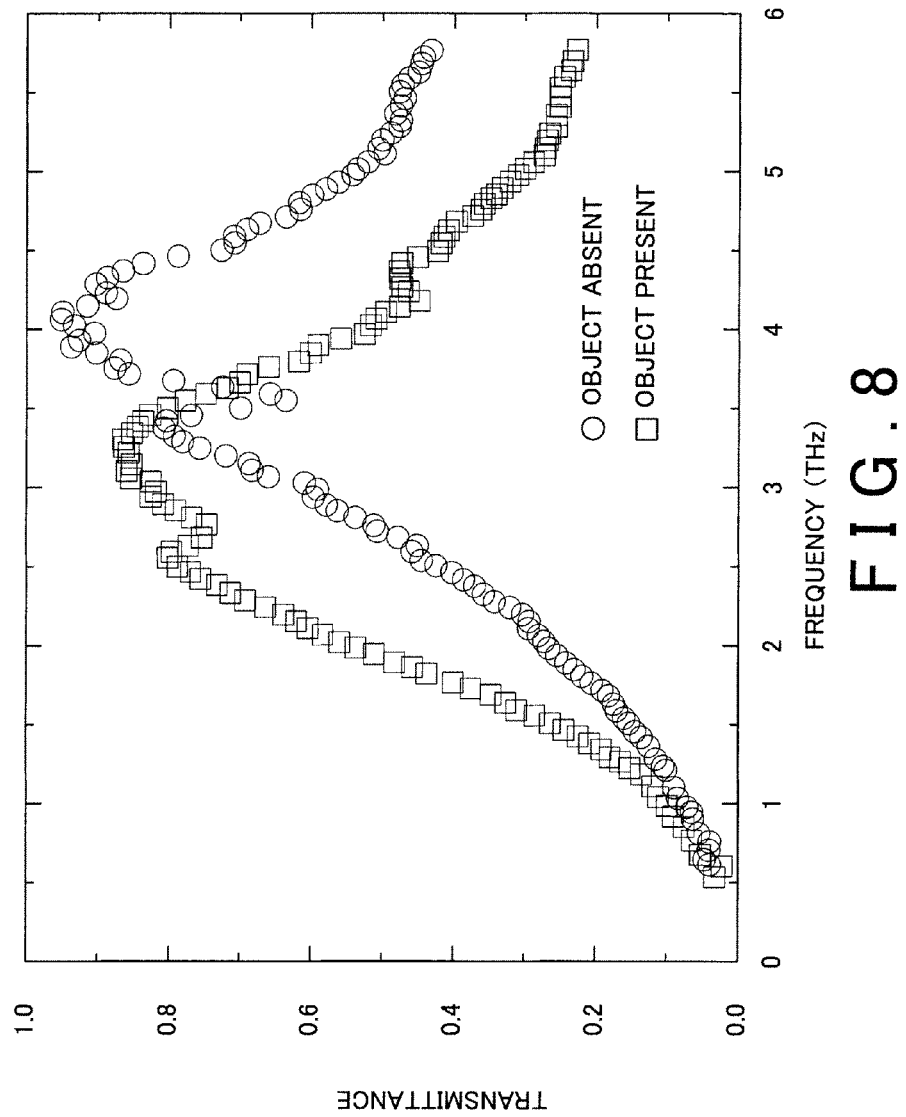
FIG. 8 is a graph illustrating the peak and dip shifts of the frequency characteristics, which are caused by whether the object 210 is present or not.

FIG. 8 is a graph illustrating a shift of a dip in the frequency characteristics of transmittance, which is caused by whether or not the object 210 is present. As seen from FIG. 8, when the object 210 is absent, the measured frequency characteristics of the transmittance of the space arrangement structure 110 also have a peak and a dip. When the frequency characteristics of the transmittance are similarly measured with a vegetable oil being directly attached to the space arrangement structure 110, the peak and dip of the frequency characteristics are both shifted to the left in the drawing. Here, since the dip is steeper than the peak, comparing the positions of the dip can more easily tell whether or not a change occurs and the amount of the change. As discussed above, the exemplary embodiment of the present invention can improve the effective detection accuracy of the terahertz wave method for measuring the characteristics of the object 210. Since the change can be detected easily with the above-described method, the exemplary embodiment of the present invention enables unskilled people to easily detect the change. This advantage can expand the applications of the characteristics measuring technique using terahertz waves.

Figure 9:
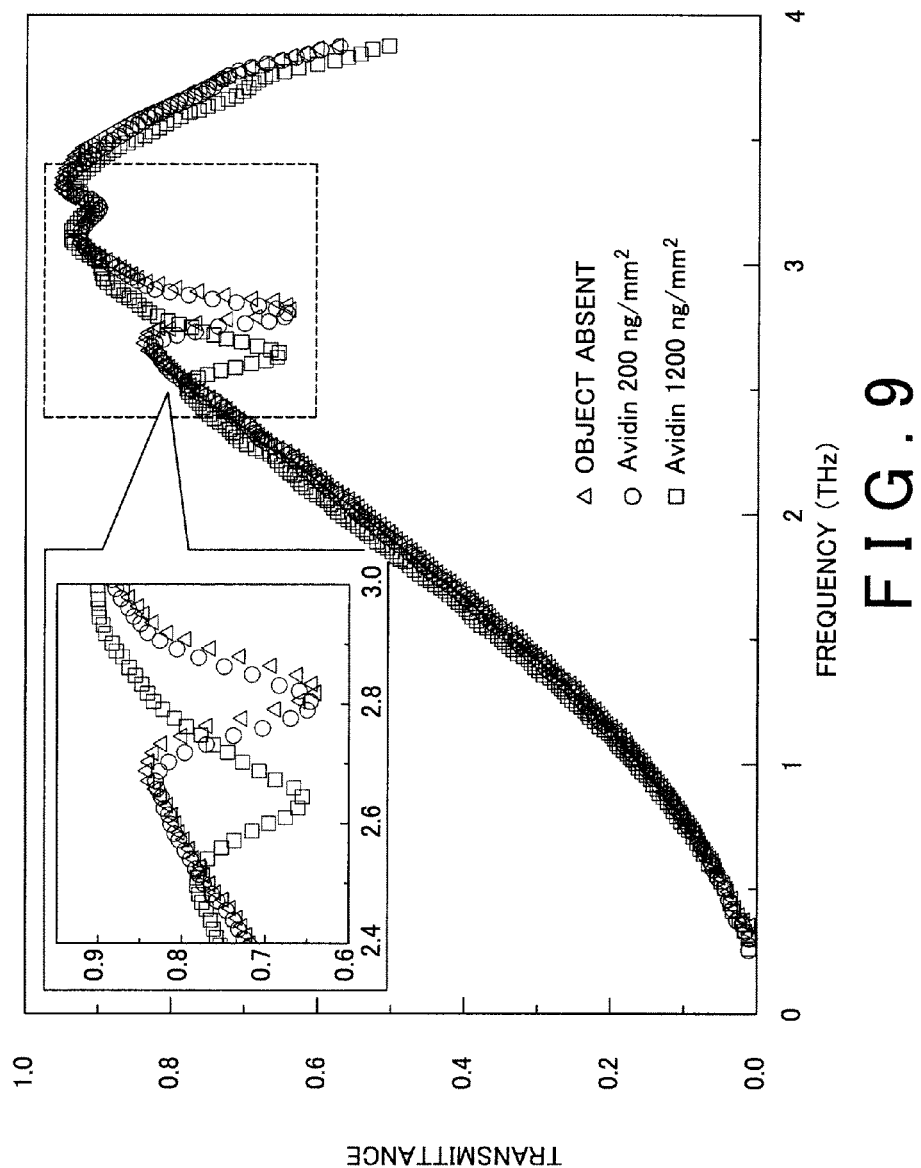
FIG. 9 is a graph illustrating peak and dip shifts of frequency characteristics of transmittance, which are caused by changing the object 210.

FIG. 9 is a graph showing a shift of a dip in frequency characteristics of transmittance, which is caused by changing the object 210. In this example, the support film 120 is immersed with a small amount of avidin, which is the object 210. Here, avidin is one type of protein used in immunoassay.

As seen from FIG. 9, when the object 210 is absent, when avidin of 200 ng/mm$^2$ is provided as the object 210, and when avidin of 1200 ng/mm$^2$ is provided as the object 210, the peak and the dip are positioned differently in the respective measurement results. Here, since the peak has a relatively broad distribution, it is particularly difficult to distinguish the measurement result obtained when the object 210 is absent from the measurement result obtained when the avidin of 200 ng/mm$^2$ is provided. On the other hand, the dip is steep and thus can be used to effectively and accurately evaluate the measurement results.

Third Embodiment

Figure 10:
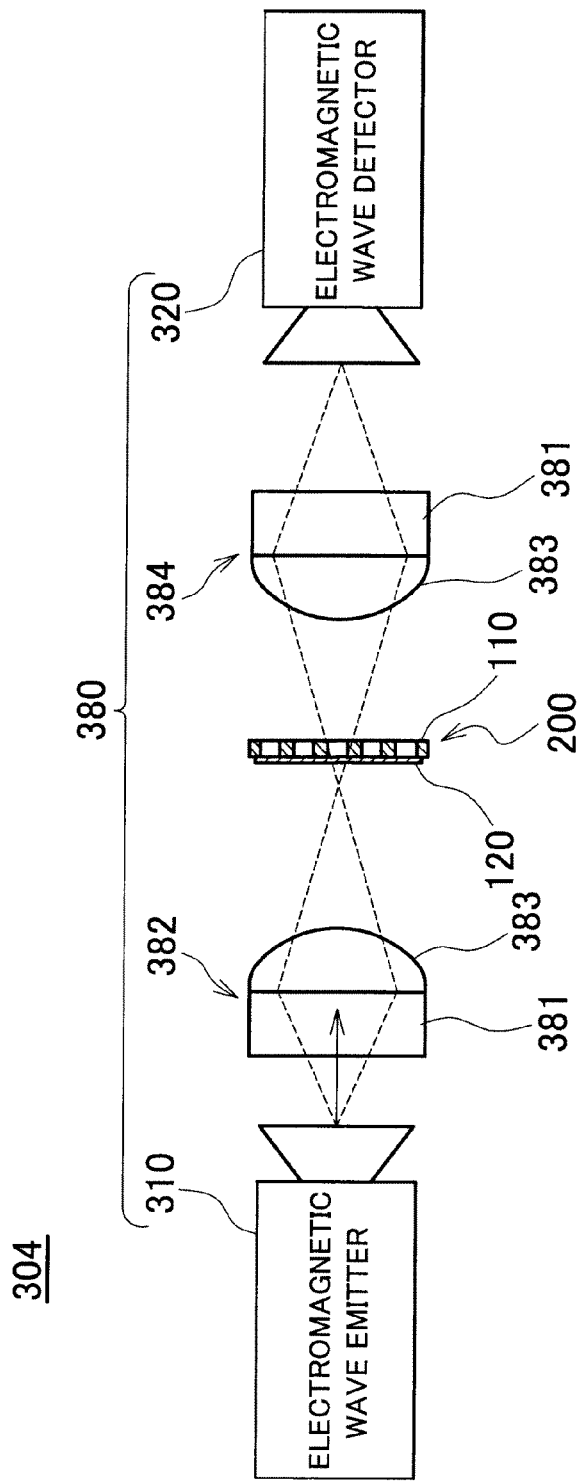
FIG. 10 schematically illustrates the configuration of an optical system 380 in a measuring apparatus 304 relating to a further different exemplary embodiment.

FIG. 10 schematically illustrates the configuration of an optical system 380 of a measuring apparatus 304 relating to a further different exemplary embodiment. Since the electromagnetic wave emitter 310, electromagnetic wave detector 320, analyzing section 350, and display 360 have the same configurations as in the measuring apparatus 300, FIG. 10 does not show some of these constituents.

As shown in FIG. 10, the measuring apparatus 304 is different from the measuring apparatus 300 shown in FIG. 3 in that the optical system 380 has compound lenses 382 and 384 in place of the collimating lenses 332 and 334. Apart from this feature, the measuring apparatus 304 is the same as the measuring apparatus 300 shown in FIG. 3, and the explanation is not repeated here.

FIG. 11 is a perspective view illustrating the shapes of the compound lenses 382 and 384 used in the measuring apparatus 304 shown in FIG. 10. As shown in FIG. 11, each of the compound lenses 382 and 384 is formed by combining together a horizontal collimating portion 381 and a vertical light collecting portion 383. The horizontal collimating portion 381 is a cylindrical surface having a vertical axis and the vertical light collecting portion 383 is a cylindrical surface having a horizontal axis in the drawing.

With such a configuration, the compound lens 382, in the horizontal direction, converts the electromagnetic waves from the electromagnetic wave emitter 310 into parallel beams of light having the same width as the electromagnetic waves which are incident on the compound lens 382 and, in the vertical direction, collects the electromagnetic waves from the electromagnetic wave emitter 310 towards the focus point. Accordingly, on the focus point of the vertical light collecting portion 383, the electromagnetic waves are shaped like a linear beam extending along a straight line perpendicular to the plane of the paper.

This linear beam is incident on the space arrangement structure 110 of the prepared slide 200 at an angle. Therefore, the measured frequency characteristics of the transmittance include an evident dip waveform, as described with reference to the second embodiment. Consequently, the third embodiment makes it possible to easily find a slight change in the frequency characteristics that is caused by the object 210, which is, together with the space arrangement structure 110, irradiated with the electromagnetic waves.

In the third embodiment, the linear beam is formed so as to extend in the horizontal direction, for example. The linear beam, however, may extend in any other direction, as long as the electromagnetic waves are incident on the plane in which the spaces 112 of the space arrangement structure 110 are arranged at the incidence angle α.

In the above-described measuring apparatus 304, the space arrangement structure 110 supporting the object 210 is positioned between the electromagnetic wave emitter 310 and the electromagnetic wave detector 320 in such a manner that the plane containing the spaces 112 is orthogonal to the straight line connecting together the electromagnetic wave emitter 310 and the electromagnetic wave detector 320, and the electromagnetic waves emitted from the electromagnetic wave emitter 310 are converged into a straight line that contains a single point on the straight line connecting together the electromagnetic wave emitter 310 and the electromagnetic wave detector 320 and is orthogonal to the straight line connecting together the electromagnetic wave emitter 310 and the electromagnetic wave detector 320. With such a configuration, even when the space arrangement structure 110 itself is fixed upright, a change in the measurement result can be easily detected similarly to the case where the space arrangement structure 110 is arranged at an angle. The above-described measuring apparatus 304 can be realized by replacing the collimating lenses 332 and 334 of the measuring apparatus 300 with the compound lenses 382 and 384. Therefore, the above-described advantage can be achieved without significantly changing the measuring apparatus 300.

Although some aspects of the present invention have been described by way of exemplary embodiments, it should be understood that those skilled in the art might make many changes and substitutions without departing from the spirit and the scope of the present invention which is defined only by the appended claims.

The claims, specification and drawings describe the processes of an apparatus, a system, a program and a method by using the terms such as operations, procedures, steps and stages. When a reference is made to the execution order of the processes, wording such as "before" or "prior to" is not explicitly used. The processes may be performed in any order unless an output of a particular process is used by the following process. In the claims, specification and drawings, a flow of operations may be explained by using the terms such as "first" and "next" for the sake of convenience. This, however, does not necessarily indicate that the operations should be performed in the explained order.

The invention claimed is:

1. A measuring apparatus comprising:
a space arrangement structure that includes space regions surrounded by conductors in a plane;
an electromagnetic wave emitter that emits electromagnetic waves towards an object held by the space arrangement structure, wherein the electromagnetic waves emitted from the electromagnetic wave emitter towards the space arrangement structure are incident on the plane containing the space regions at an angle;
an electromagnetic wave detector that detects the electromagnetic waves that have passed through the space arrangement structure; and
an analyzer configured to measure characteristics of the object by comparing a position of a dip in a waveform of measured frequency characteristics of a transmittance of the space arrangement structure when the object is absent with a position of a dip in a waveform of measured frequency characteristics of a transmittance of the space arrangement structure when the object is present, wherein
the space arrangement structure holding the object is placed between the electromagnetic wave emitter and the electromagnetic wave detector in such a manner that the plane containing the space regions is orthogonal to a straight line connecting together the electromagnetic wave emitter and the electromagnetic wave detector, and
the electromagnetic waves emitted from the electromagnetic wave emitter are converged towards a single point on the straight line after the electromagnetic wave emitter and before the space arrangement structure and the object.

2. The measuring apparatus as set forth in claim 1, wherein the analyzer measures the characteristics of the object based on a shift amount between the position of the dip in the waveform of the measured frequency characteristics of the transmittance of the space arrangement structure when the object is absent and the position of the dip in the waveform of measured frequency characteristics of the transmittance of the space arrangement structure when the object is present.

3. The measuring apparatus as set forth in claim 1, wherein an incidence angle of the electromagnetic waves with respect to the plane containing the space regions is set no more than 10 degrees.

4. A measuring apparatus comprising:
a space arrangement structure that includes space regions surrounded by conductors in a plane;
an electromagnetic wave emitter that emits electromagnetic waves towards an object held by the space arrangement structure, wherein the electromagnetic waves emitted from the electromagnetic wave emitter towards the space arrangement structure are incident on the plane containing the space regions at an angle;
an electromagnetic wave detector that detects the electromagnetic waves that have passed through the space arrangement structure; and
an analyzer configured to measure characteristics of the object by comparing a position of a dip in a waveform of measured frequency characteristics of a transmittance of the space arrangement structure when the object is absent with a position of a dip in a waveform of measured frequency characteristics of a transmittance of the space arrangement structure when the object is present, wherein
the space arrangement structure holding the object is placed between the electromagnetic wave emitter and the electromagnetic wave detector in such a manner that the plane containing the space regions is orthogonal to a straight line connecting together the electromagnetic wave emitter and the electromagnetic wave detector, and
the electromagnetic waves emitted from the electromagnetic wave emitter are converged into a straight line that (i) contains a single point after the electromagnetic wave emitter and before the space arrangement structure and the object on the straight line connecting together the electromagnetic wave emitter and the electromagnetic wave detector and (ii) is orthogonal to the straight line connecting together the electromagnetic wave emitter and the electromagnetic wave detector.

5. The measuring apparatus as set forth in claim 4, wherein an incidence angle of the electromagnetic waves with respect to the plane containing the space regions is set no more than 10 degrees.

6. The measuring apparatus as set forth in claim 4, wherein the analyzer measures the characteristics of the object based on a shift amount between the position of the dip in the waveform of the measured frequency characteristics of the transmittance of the space arrangement structure when the object is absent and the position of the dip in the waveform of measured frequency characteristics of the transmittance of the space arrangement structure when the object is present.

7. A measuring method comprising:
emitting electromagnetic waves towards an object held by a space arrangement structure including space regions surrounded by conductors in a plane, wherein the electromagnetic waves emitted from the electromagnetic wave emitter towards the space arrangement structure are incident on the plane containing the space regions at an angle;
detecting the electromagnetic waves that have passed through the space arrangement structure; and
measuring characteristics of the object by comparing a position of a dip in a waveform of measured frequency characteristics of a transmittance of the space arrangement structure when the object is absent with a position of a dip in a waveform of measured frequency characteristics of a transmittance of the space arrangement structure when the object is present, the dip in each waveform created due to the incidence angle of the electromagnetic waves with respect to a normal line of the plane containing the space regions.

8. The measuring apparatus as set forth in claim 7, wherein an incidence angle of the electromagnetic waves with respect to the plane containing the space regions is set no more than 10 degrees.

9. The measuring method as set forth in claim 7, wherein the measuring comprises measuring the characteristics of the object based on a shift amount between the position of the dip in the waveform of the measured frequency characteristics of the transmittance of the space arrangement structure when the object is absent and the position of the dip in the waveform of measured frequency characteristics of the transmittance of the space arrangement structure when the object is present.

10. The measuring method as set forth in claim 7, wherein
the emitting is performed by using an electromagnetic wave emitter,
the detecting is performed by using an electromagnetic wave detector, and
the space arrangement structure holding the object is placed between the electromagnetic wave emitter and the electromagnetic wave detector in such a manner that the plane containing the space regions is at an angle with respect to a straight line connecting together the electromagnetic wave emitter and the electromagnetic wave detector.

11. The measuring method as set forth in claim 7, wherein
the emitting is performed by using an electromagnetic wave emitter,
the detecting is performed by using an electromagnetic wave detector,
the space arrangement structure holding the object is placed between the electromagnetic wave emitter and the electromagnetic wave detector in such a manner that the plane containing the space regions is orthogonal to a straight line connecting together the electromagnetic wave emitter and the electromagnetic wave detector, and
the electromagnetic waves emitted from the electromagnetic wave emitter are converged towards a single point on the straight line.

12. The measuring apparatus as set forth in claim 7, wherein
the emitting is performed by using an electromagnetic wave emitter,
the detecting is performed by using an electromagnetic wave detector,
the space arrangement structure holding the object is placed between the electromagnetic wave emitter and the electromagnetic wave detector in such a manner that the plane containing the space regions is orthogonal to a straight line connecting together the electromagnetic wave emitter and the electromagnetic wave detector, and
the electromagnetic waves emitted from the electromagnetic wave emitter are converged into a straight line that (i) contains a single point on the straight line connecting together the electromagnetic wave emitter and the electromagnetic wave detector and (ii) is orthogonal to the straight line connecting together the electromagnetic wave emitter and the electromagnetic wave detector.

13. The measuring method as set forth in claim 7, wherein the dip in each waveform becomes deeper as the incidence angle increases.

14. The measuring method as set forth in claim 7, wherein the dip is steeper than the steepest peak in each waveform.

* * * * *